United States Patent
van Kessel

(10) Patent No.: US 7,333,188 B2
(45) Date of Patent: Feb. 19, 2008

(54) METHOD AND APPARATUS FOR REAL-TIME MEASUREMENT OF TRACE METAL CONCENTRATION IN CHEMICAL MECHANICAL POLISHING (CMP) SLURRY

(75) Inventor: Theodore G. van Kessel, Millbrook, NY (US)

(73) Assignee: International Business Machines Corporation, Armonk, NY (US)

( * ) Notice: Subject to any disclaimer, the term of this patent is extended or adjusted under 35 U.S.C. 154(b) by 407 days.

(21) Appl. No.: 10/953,380

(22) Filed: Sep. 30, 2004

(65) Prior Publication Data

US 2006/0072701 A1    Apr. 6, 2006

(51) Int. Cl.
*G01N 21/00* (2006.01)
(52) U.S. Cl. ........................................ 356/72
(58) Field of Classification Search ............... 356/72
See application file for complete search history.

(56) References Cited

U.S. PATENT DOCUMENTS

| | | | | |
|---|---|---|---|---|
| 5,164,975 | A * | 11/1992 | Steinmeyer | 378/85 |
| 5,561,520 | A * | 10/1996 | Williams | 356/335 |
| 5,574,232 | A * | 11/1996 | Davidson et al. | 73/864.81 |
| 6,246,474 | B1 * | 6/2001 | Cerni et al. | 356/335 |
| 6,275,290 | B1 * | 8/2001 | Cerni et al. | 356/335 |
| 6,709,311 | B2 * | 3/2004 | Cerni | 451/5 |
| 2003/0032366 | A1 * | 2/2003 | Cerni | 451/5 |
| 2005/0009213 | A1 * | 1/2005 | Wang et al. | 438/5 |

* cited by examiner

*Primary Examiner*—Roy M. Punnoose
(74) *Attorney, Agent, or Firm*—McGinn, IP Law Group, PLLC; Stephen C. Kaufman, Esq.

(57) ABSTRACT

A system (and method) for real-time measurement of trace metal concentration in a chemical mechanical polishing (CMP) slurry, includes an electromagnetic radiation flow cell carrying a CMP slurry, a slurry pickup head coupled to the flow cell, and an analyzer for measuring properties of the slurry flowing through the flow cell.

29 Claims, 5 Drawing Sheets

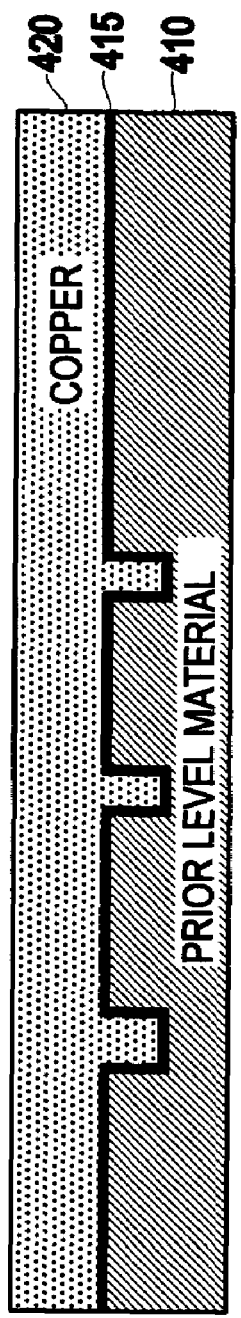
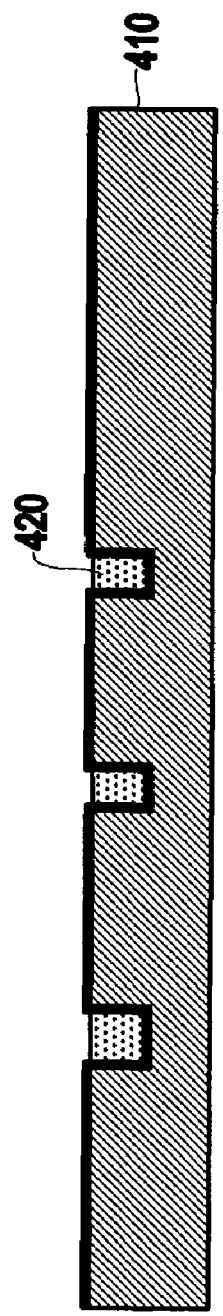
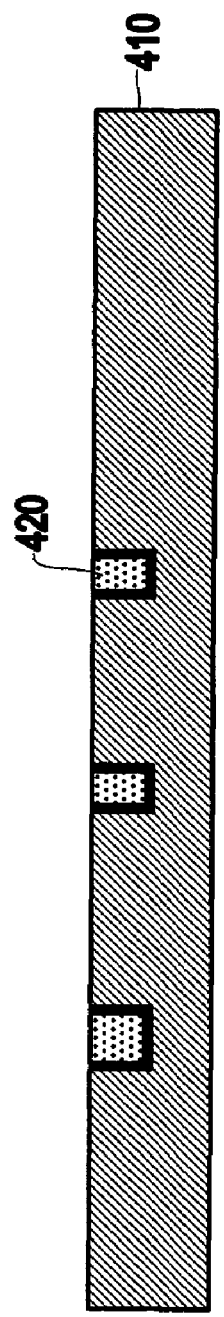
FIG.4A
FIG.4B
FIG.4C

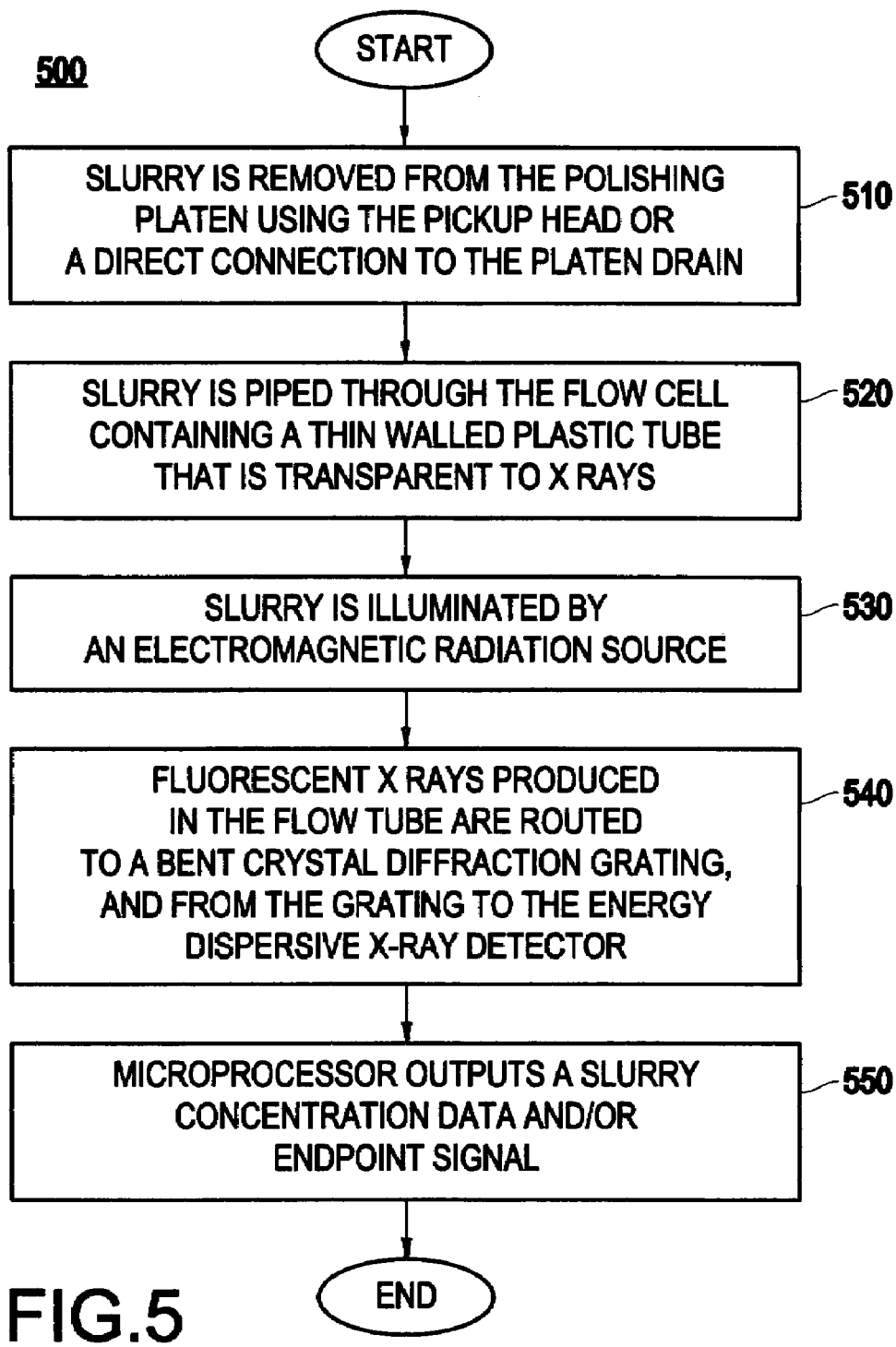

METHOD AND APPARATUS FOR REAL-TIME MEASUREMENT OF TRACE METAL CONCENTRATION IN CHEMICAL MECHANICAL POLISHING (CMP) SLURRY

BACKGROUND OF THE INVENTION

1. Field of the Invention

The present invention generally relates to a method and apparatus for measuring a material in a slurry during a polish process, and more particularly to a method and apparatus for accurately monitoring polish processes by measuring a removed metal concentration in the slurry.

2. Description of the Related Art

Copper and Tantalum liner polish operations typical of current copper back end of line (BEOL) (and aluminum BEOL in some cases) interconnect layers involve the bulk removal of metal by chemical mechanical polishing (CMP) on processed semiconductor wafers.

In operation, there is some level of interest to which the designer wishes to make connections. To do so, an oxide is deposited over the level, lines and holes (vias) are made in the oxide, patterned therein and extending down to the level of interest (e.g., the layer to which the connections are to be made). Then, a liner (e.g., formed of tungsten, tantalum, etc.) is formed over the wafer surface and in each of the holes, and then a copper layer is electroplated over the structure. Thereafter, the copper layer is polished back until the liner is exposed everywhere except where there are trenches or holes. Thus, all that is left is the interconnect wires, and the bulk copper is removed.

A condition arises in that, as the final stage of polishing is reached, the copper concentration in the slurry drops, as the relatively thin liner (which has a possibly different selectivity to the polish) is reached, and thus the liner becomes present in the slurry (e.g., because the liner is now being ground). The liner components in the slurry typically exist in fairly low concentrations (e.g., about 30 ppm to about 50 ppm). Thus, detection is somewhat difficult. It is desirable at this point to stop the copper polish before a large amount of liner has been removed. Prior to the invention, no method has existed which could precisely stop the polishing process to avoid polishing the liner.

Thus, the correct performance of these process operations depend on each polishing step being stopped precisely as the material of each layer is depleted.

Prior to the present invention, no conventional method has been developed which can achieve such precise stopping.

Further, it is noted that thermal endpoint methods exist which take advantage of the evolved heat due to friction. As the liner is reached, the friction between the polish pad and wafer in the presence of slurry changes. This results in a sensible change in temperature in some polish operations. Due to the thermal masses involved and the thermal time constant of the system, it takes a certain amount of time to sense the change (typically several seconds or more). Thus, the thermal endpoint method does not work for all processes.

SUMMARY OF THE INVENTION

In view of the foregoing and other exemplary problems, drawbacks, and disadvantages of the conventional methods and structures, an exemplary feature of the present invention is to provide a method and structure in which real-time measurement of predetermined trace material (e.g., metal) concentration in a chemical mechanical polishing (CMP) slurry can be performed.

In a first aspect of the present invention, a system (and method) for real-time measurement of trace metal concentration in a chemical mechanical polishing (CMP) slurry, includes an electromagnetic radiation flow cell for carrying a CMP slurry, a slurry pickup head coupled to the flow cell, and an analyzer for measuring the concentration of a material of interest in the slurry flowing through the flow cell.

With the unique and unobvious method and structure of the invention, the waste slurry is pumped from a pickup head on a platen (or directly from a platen drain) through a flow cell where a concentration of a desired metal is measured in real-time using, in a preferred example, x-ray fluorescence methods. The flow cell is sensitive to concentrations in the ~30 ppm range, and responds on the order of seconds or tens of seconds.

Thus, with the invention, as a given layer of surface metal is depleted or encountered by CMP polishing, the concentration of metal monitored will change. Sensing this change enables the process endpoint to be detected and the process monitored.

Additionally, process monitoring advantages include the feedback of the actual top surface metal thickness to prior level deposition processes and the uniformity of thickness across the wafer.

BRIEF DESCRIPTION OF THE DRAWINGS

The foregoing and other exemplary purposes, aspects and advantages will be better understood from the following detailed description of an exemplary embodiment of the invention with reference to the drawings, in which:

FIGS. 4A-4C illustrate wafer surface films during CMP copper and liner polishing operations according to the present invention, and more specifically:

FIG. 4A illustrates a side view of a wafer surface before copper polishing;

FIG. 4B illustrates a side view of the wafer surface after copper polishing and before liner polishing; and FIG. 4C illustrates a side view of the wafer surface after liner polishing; and FIG. 5 illustrates a flowchart of a method 500 according to the present invention.

DETAILED DESCRIPTION OF EXEMPLARY EMBODIMENTS OF THE INVENTION

Figure 1:
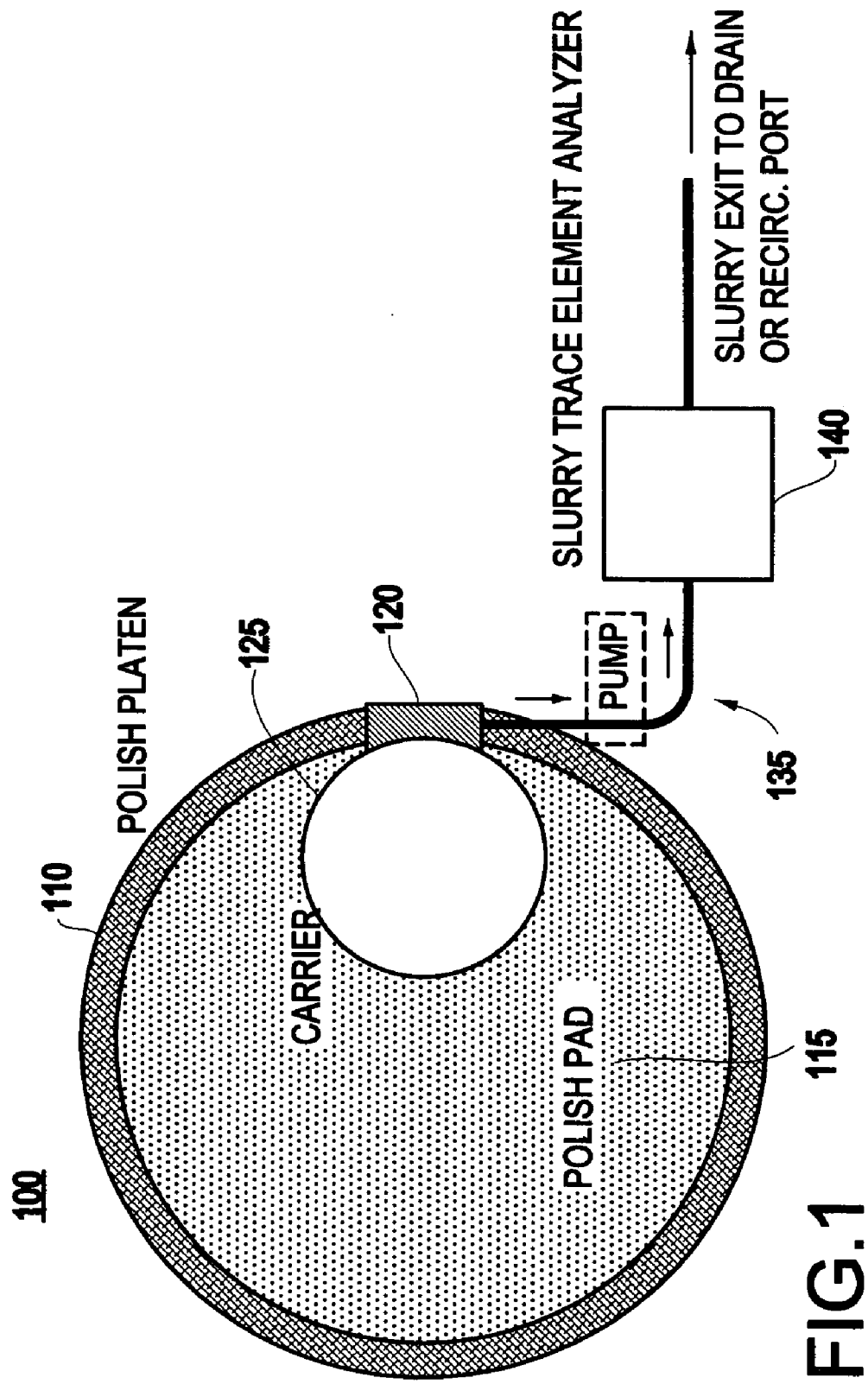
FIG. 1 illustrates a flow diagram of a system 100 according to the present invention.

Referring now to the drawings, and more particularly to FIGS. 1-5, there are shown exemplary embodiments of the method and structures according to the present invention.

Generally, as discussed briefly above, the present invention allows sampling of the slurry immediately (and directly) coming off of the polishing pad. Then, the sample is pumped through a flow cell in which the invention has constructed a very sensitive X-ray detector. The X-ray detector is for detecting the fluorescent X rays from a material of interest (e.g., copper, tantalum, titanium, aluminum, tungsten, etc.; any metal of interest). Each of these elements has a unique, characteristic fluorescent X-ray emission.

Thus, if these elements are bombarded with X rays, then the elements will fluoresce, and will emit a characteristic X ray at a certain wavelength that is unique. Such a unique wavelength can be used to identify the particular material in the presence of other different materials. Ideally, a system should be provided which provides a fairly rapid response. That is, polishing operations typically occur in tens of seconds, or fractions of minutes. Thus, a system is desirable which provides a rapid, crisp response in seconds or less.

With X-ray operations, detection essentially requires counting. Conventionally, X-ray detectors in general are typically limited, due to electronic considerations, etc., to a rate of about 50,000 counts/second. Typically, an "accurate" count (e.g., a count made with certainty that one knows the number) is proportional approximately to the square root of the total number of counts.

Thus, if one wishes to be accurate to within 1%, then 10,000 counts must be obtained. Hence, in the optimal case, the invention excludes all photons but those in the energy range of interest for that element.

For example, assuming a 10 keV emission line of interest, only the photons at 10 keV are desired to be counted. Hence, the sample is being illuminated with this broad sample of X rays. As a result, all of the elements in the sample are fluorescing, not just the ones of interest. If one were to simply position a counter near the sample, then all of the counts from all of the elements would be present. This is problematic since only a fraction of a percent of the counts is from the element of interest. Hence, if all that is done is to count the X rays coming directly off of the sample after illuminating it, then to obtain an accurate count (given 50,000 counts/second) would take a prohibitively long time.

An exemplary embodiment of the present invention solves the above and other problems by integrating a bent crystal diffraction grating into the design. The diffraction grating spatially spreads a partially collimated beam of photons according to their energy (similarly to a prism spreading a beam of light). By partially collimating the fluorescent emissions coming from the flow cell, directing these emissions into the diffraction grating and into an X-ray detector placed to receive the photos of the desired energy, all but the desired characteristic fluorescent emissions are detected.

Generally, a SiLi detector is used in combination with a multichannel analyzer. The multichannel analyzer is understood to include a computer and electronics for pulse shaping, analog digital conversion, channel counting and binning etc., and the control and analysis software necessary to reduce the raw detector signal to a usable output signal (material concentration and endpoint). This configuration combines wavelength dispersive and energy dispersive methods of X-ray spectroscopy to achieve the desired result.

In the case where speed is less critical, the bent crystal can be excluded and a detector with multichannel analysis capability used by itself.

That is, invention pumps waste slurry from a pickup head on a platen or directly from a platen drain through a flow cell where a concentration of a desired metal is measured in real time by measuring its X-ray fluorescence. The flow cell is sensitive to concentrations in the ~30 ppm range, and responds on the order of tens of seconds or seconds.

Thus, with the invention, as a given layer of surface metal is being depleted by CMP polishing, the concentration of metal monitored will drop. Sensing this allows precisely stopping the polishing operations.

Exemplary Embodiment

FIG. 1 illustrates a flow diagram of an apparatus 100 according to the present invention.

Specifically, slurry is removed from a polishing platen 110 (having a polishing pad 115) using a pickup head 120 or a direct connection to the platen drain. A carrier 125 is adjacent the slurry pickup head 120. Then, the slurry is piped through a flow cell contained in the trace element analyzer 140 shown in FIG. 1 containing a thin-walled plastic tube that is transparent to X rays (illustrated by arrows in FIG. 2).

A radiation source 225 (e.g., X ray source 225 not shown in FIG. 1, but illustrated in FIG. 2) illuminates the tube (slurry line 230). The X-ray source is set to produce X rays up to 30 keV. The X-ray photons traveling through the tube produce fluorescence in the metal atoms contained in the slurry.

Figure 2:
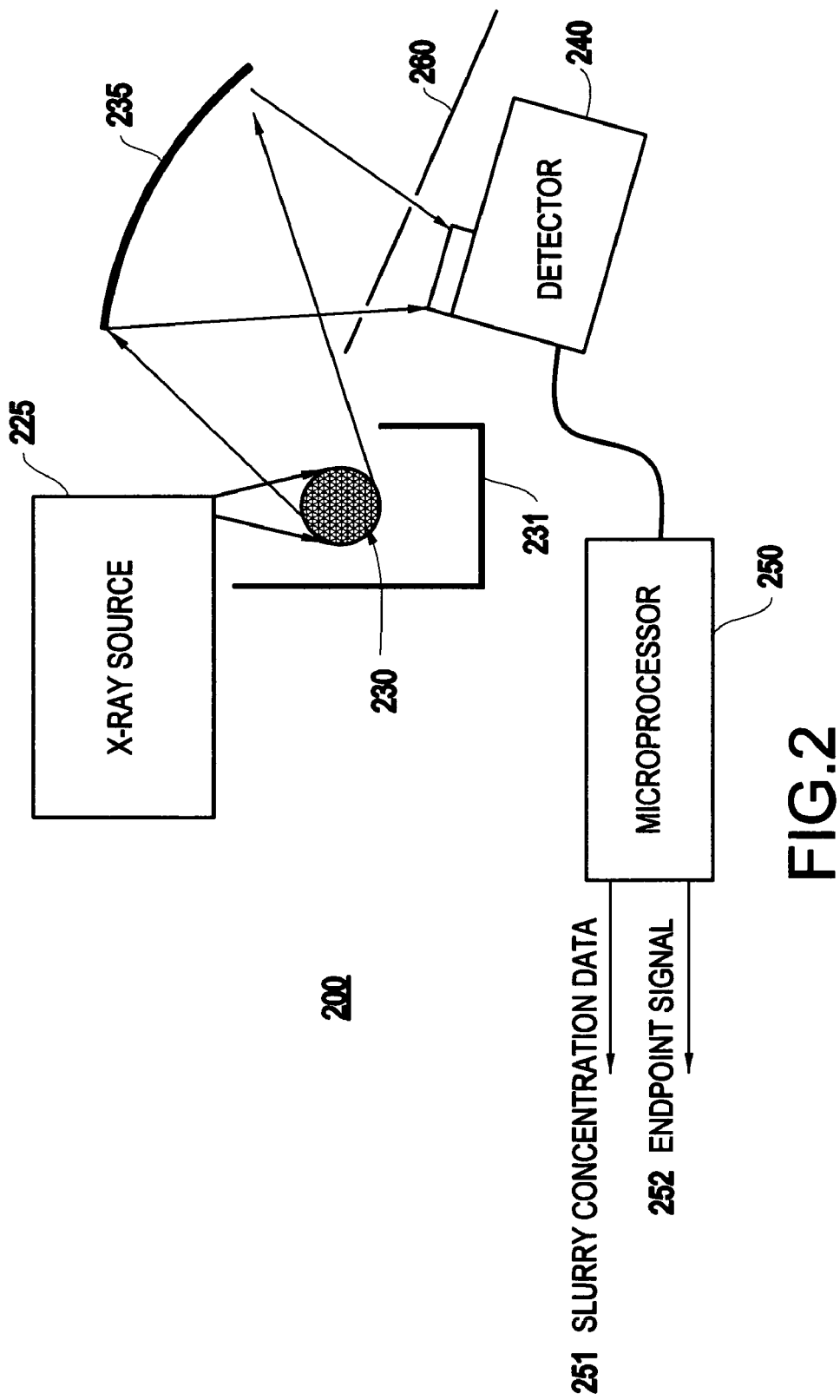
FIG. 2 illustrates a system block diagram of a slurry trace element analyzer 200 according to the present invention.

The fluorescent X rays, produced in the flow tube 230, illuminate a bent crystal illuminate diffraction grating (shown in greater detail in FIG. 2 at reference numeral 235), and are diffracted from there to an energy dispersive X-ray detector (shown in greater detail in FIG. 2 at reference numeral 240). Counts from the detector are monitored and interpreted by a computer (microprocessor) 250 which also connects to the polisher to provide the signal to notify it when endpoint is reached. In the exemplary, non-limiting embodiment, a SiLi detector is used. Other detectors could be used including scintillation/photomultiplier detectors, etc. Then, the slurry exits to a drain or a recirculation port.

The pickup head provides pumping action under normal circumstances of platen rotation and where the sensor is located below the level of the platen due to the Bernoulli effect. Optionally, the system may include a pump 130 between the pickup head 120 and the trace element analyzer 140 to ensure precise flow or more convenient placement of the analyzer.

It is important to the function of the device that it be able to respond with a time constant on the order of seconds (or preferably tenths of seconds) As mentioned above, typical energy dispersive X-ray detector will count a maximum of 50,000 counts per second. To achieve a desired response time, approximately 100 to 1000 counts per second should be measured in the region of interest for an accurate count.

FIG. 2 illustrates a system diagram of a slurry trace element analyzer 200 (e.g., similar to that of analyzer 140 in FIG. 1) according to the present invention.

Again, slurry is removed from a polishing platen (having a polishing pad) using a pickup head or a direct connection to the platen drain. Then, the slurry is piped through a flow cell 230 (e.g., a slurry flow tube) containing a thin-walled plastic tube that is transparent to X rays.

An X-ray source 225 illuminates the tube 230. Again, the X-ray source 225 is set to produce X rays up to 30 keV. The X-ray photons traveling through the tube 230 produce fluorescence in the metal atoms contained in the slurry.

A detector shield 231 is positioned adjacent the flow tube 230 for shielding a detector 240. The shield 231 may be comprised of sheet metal or like material having suitable stopping power for the energy range of the source and is shaped to exclude X-ray scatter for all but the desired path. It is noted that this is understood to include apertures and slits at multiple points in the beam path.

The fluorescent X rays so produced in the flow tube 230 are routed to a bent crystal diffraction grating 235. Many gratings can be used. The particular grating is chosen to diffract photons at the particular X-ray line energy at the correct angle to the detector and exclude adjacent and unwanted X-ray lines.

From the grating 235, X rays are diffracted to the detector 240 (e.g., an energy dispersive X-ray detector such as a SiLi detector or the like) which is understood to contain an entrance aperture or slit.

The detector 240 is operatively coupled to a microprocessor 250 with the appropriate electronics for pulse shaping, analog-to-digital conversion, multichannel analysis, and control and signal interpretation software necessary to output slurry concentration data 251 and/or an endpoint signal 252. In a different embodiment, the source 225, grating 235, and detector 240 are replaced by visible wavelength optics to detect a change in color, and thus could function similarly to a spectrometer or the like. Indeed, the slurry containing some of the trace elements (e.g., metals) may have a completely different color (e.g., be visibly different) from a slurry which does not, even if the concentration is very low.

Figure 3:
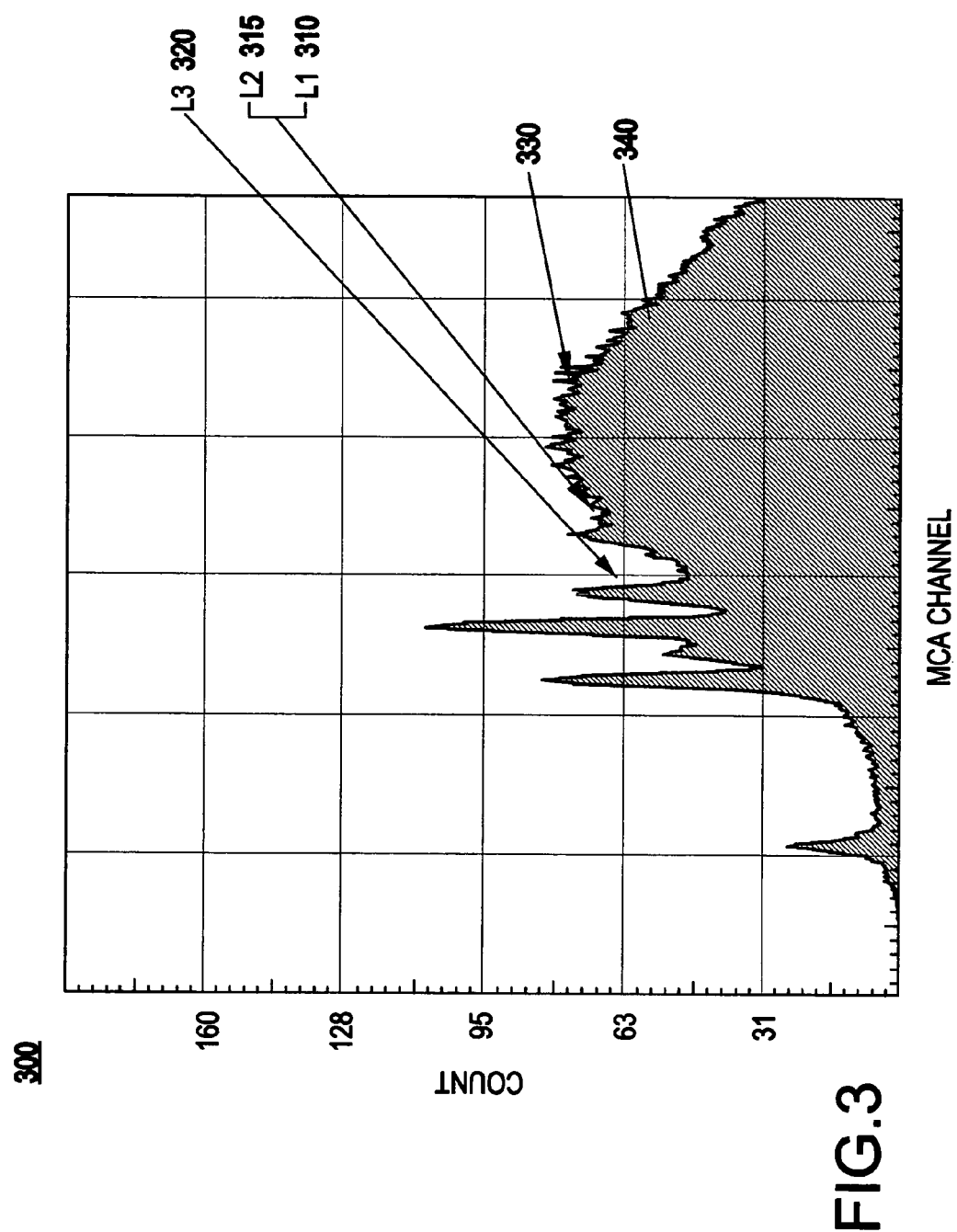
FIG. 3 illustrates a slurry spectra 300 of the slurry trace element analyzer according to the present invention.

Fluorescent X rays at many energies are produced in the flow tube 230. FIG. 3 shows such a spectrum with, for example, the tantalum lines shown.

That is, FIG. 3 shows the counts in relation to the multichannel analyzer (MCA) channel. In FIG. 3, a raw X-ray fluorescence spectra for slurry with and without a Ta liner. The X-ray source was at about 20.0 kV at a current of about 67 μA.

The Ta peaks (eV)(for L1/L2 spectroscopic levels) are 11681.5 and 11136.1, respectively, and are shown at reference numerals 310 and 315. The Ta peak for L3 was 9881.1 and is shown at reference numeral 320. The waveform for slurry with the Ta liner is shown at reference numeral 330, whereas the waveform for slurry only is shown at reference numeral 340.

In this example, assuming the invention is interested in K line and L line emissions characteristic of the element of interest, the invention employs the bent crystal analyzer 235 to achieve this selection.

That is, by adjusting the angle of the crystal 235, only photons with the energy of interest are directed to the detector 240, while others are blocked by an optional baffle 260.

The baffle 260 could be a slit or an aperture allowing certain photons to be passed therethrough to the detector, but which blocks all other photons. This allows the invention to utilize most of the detector counting bandwidth to count photons of interest. Again, the baffle/slit is optional, as it is noted that the tube size also effectively defines the spot size.

The counts per unit time at the fluorescent energy is proportional to the concentration of the element. By counting the number of photons at the energy of interest per unit time, the invention can monitor the concentration of the desired material sufficiently for endpoint detection purposes. This data may be constructed by a computer system (e.g., microprocessor 250) attached to the X-ray detector 240.

Thus, the invention only counts the photons in the wavelength range of interest, and thus if 10,000 counts are needed, then, in principle, one can obtain five measurements per second (assuming that there are enough photons to do it), which is purely a function of how bright the source is. Hence, a brighter source could be provided. Thus, the invention provides an efficient instrument which counts only the photons in the wavelength of interest, and such can be detected.

The effect of the CMP polishing process on the surface films of a wafer is exemplarily shown in FIGS. 4A-4C for the copper 420 and copper liner 415 CMP polish process. A prior level material 410 is provided, having the liner 415 formed thereon, followed by the copper layer 420 deposition.

It is noted that as each layer of copper 420 or liner (e.g., Ta, etc.) 415 is removed, there will be an abrupt change in the amount of surface metal flowing into the slurry as the polish reaches the interface between the material being polished and the next material. The resultant change in concentration of this surface metal in the slurry is what the inventive sensor monitors.

FIG. 5 illustrates a method 500 according to the present invention for real-time measurement or trace metal concentration in a CMP slurry.

In step 510, slurry is removed from the polishing platen using the pickup head or a direct connection to the platen drain.

In step 520, the slurry is piped through the flow cell containing a thin walled plastic tube that is transparent to x-rays In step 530, the slurry in the tube is illuminated by a radiation source (e.g., an X-ray source will be assumed in the present exemplary embodiment). The x-ray photons traveling through the tube produce fluorescence in the metal atoms contained in the slurry.

In step 540, the fluorescent X rays produced in the flow tube are routed to a bent crystal diffraction grating, and from the grating to the energy dispersive X-ray detector.

In step 550, the microprocessor outputs a slurry concentration data and/or an endpoint signal.

As described above, the method of the invention allows the user to know the progress of the CMP process, and allows the user to control the process. Thus, for example, the invention allows stopping the CMP (e.g., grinding) process immediately (e.g., through feedback), or could allow some over-polish to occur.

Additionally, the invention is advantageous in that it allows the equipment of the system to be monitored. For example, if the slurry failed (e.g., wrong slurry in the tool, the slurry was not being delivered in the correct rate, a defective pad, etc.; each of which may be a "silent" failure), then the invention would detect the same. Thus, it would become obvious that the tool failed, thereby allowing the system to be shut down. As such, the invention provides a tool performance monitor. Hence, if one tool is finishing (or starting) at a different time than the other tools in the system (e.g., one tool is operable 5 seconds longer than others), the system can be shut down and the failure investigated/remedied.

As described above, with the unique and unobvious method and structure of the invention, the waste slurry is pumped from a pickup head on a platen or directly from a platen drain through a flow cell where a concentration of a desired metal is measured in real-time using x-ray fluorescence methods. The flow cell is sensitive to concentrations in the ~30 ppm range, and can respond on the order of seconds (or tenths of seconds).

Hence, with the invention, as a given layer of surface metal is depleted by polishing (e.g., CMP polishing), the concentration of metal monitored will drop. Sensing this drop will enable the process endpoint to be detected.

While the invention has been described in terms of several exemplary embodiments, those skilled in the art will recognize that the invention can be practiced with modification within the spirit and scope of the appended claims.

For example, the invention is not limited to X rays, but other radiation could be used. Thus, for example, a system for real-time measurement of trace metal concentration in a chemical mechanical polishing (CMP) slurry could be provided in which an optical source would be provided instead of the X-ray source, an optical flow cell for carrying a CMP slurry would be provided instead of an X-ray flow cell, a diffraction grating would be provided instead of the bent crystal analyzer, and a photodetector would be provided instead of a SiLi detector. Thus, in the above system, an optical spectrometer would be provided in place of the X-ray spectrometer.

Further, it is noted that Applicant's intent is to encompass equivalents of all claim elements, even if amended later during prosecution.

What is claimed is:

1. A system for real-time measurement of trace predetermined material concentration in a chemical mechanical polishing (CMP) slurry, comprising:
   a CMP slurry flow cell analyzer for determining at least one of x-ray transmission and x-ray fluorescent properties of a slurry flowing through the cell;
   a slurry pickup pumping head coupled to said flow cell; and
   a processor for receiving the output from said flow cell analyzer, and for interpreting measured characteristic emissions of the slurry in response to the applied radiation.

2. The system of claim 1, further comprising:
   a radiation source for illuminating said slurry.

3. The system of claim 1, wherein said analyzer includes a bent crystal analyzer.

4. The system of claim 3, wherein said analyzer further includes a detector for receiving and measuring a quantity of photons from said bent crystal analyzer.

5. The system of claim 4, wherein said detector comprises a SiLi detector.

6. The system of claim 4, wherein said processor receives an output from said detector for providing any of a slurry concentration signal and an endpoint signal.

7. The system of claim 4, further comprising:
   an electromagnetic radiation source for illuminating the flow cell, wherein photons traveling through the tube produce fluorescent rays in a predetermined material atoms contained in the slurry.

8. The system of claim 7, wherein the detector of the flow cell analyzer receives said fluorescent rays.

9. The system of claim 4, further comprising:
   a detector shield positioned adjacent the flow cell for shielding the detector from any of stray and scattered photons from other than the desired locations.

10. The system of claim 4, wherein adjustment to an angle of a crystal of the bent crystal analyzer is provided such that only photons with an energy of interest are directed to the detector.

11. The system of claim 10, further comprising:
    a baffle for allowing only predetermined ones of said photons to be passed therethrough to the detector.

12. The system of claim 1, further comprising:
    a pump coupled to said flow cell.

13. The system of claim 1, wherein said slurry is removed one of from a polishing pad using said pickup head, and a direct connection through said flow cell to a polishing pad drain.

14. The system of claim 1, wherein the slurry is piped through said flow cell, said flow cell comprising a plastic tube transparent to said electromagnetic radiation.

15. The system of claim 1, said slurry being usable by a polishing tool, wherein data representing an interpretation of the measured characteristic emissions of the slurry is output from the processor to the polishing tool.

16. The system of claim 1, wherein the system determines a process endpoint based on detected trace materials.

17. The system of claim 1, wherein the trace predetermined material concentration is measured without regard for slurry particles.

18. A slurry extraction tool, comprising: a pickup head associated with slurry; and a trace element analyzer coupled to said pickup head for analyzing said slurry.

19. The tool of claim 18, wherein said trace element analyzer comprises:
    an optical source for illuminating said slurry;
    a grating for receiving photons from said illuminated slurry; and
    a photodetector for receiving said illuminated photons from said bent crystal analyzer.

20. The tool of claim 18, further comprising:
    a pump coupled to said pickup head for pumping said slurry.

21. The tool of claim 18, wherein said trace element analyzer comprises:
    an X-ray source for illuminating said slurry;
    a bent crystal analyzer for receiving photons from said illuminated slurry; and
    a detector for receiving said illuminated photons from said bent crystal analyzer.

22. A system for real-time measurement of trace metal concentration in a chemical mechanical polishing (CMP) slurry, comprising:
    an optical flow cell for having a CMP slurry flow therethrough;
    a slurry pickup head operatively coupled to said optical flow cell;
    an x-ray source and detector configured to excite fluorescence in said flow cell and detect the resultant emission.

23. A method of real-time measurement of trace predetermined material concentration in a chemical mechanical polishing (CMP) slurry, comprising:
    illuminating a slurry in a flow cell by radiation such that radiation photons traveling through the flow cell produce fluorescence in predetermined material atoms contained in the slurry;
    analyzing the fluorescent radiation photons produced in the flow cell; and
    taking an action based on said analyzing.

24. The method of claim 23, further comprising:
    flowing slurry through the flow cell that is transparent to the radiation.

25. The method of claim 23, wherein said analyzing is performed by sending said fluorescent radiation photons to a detector via a bent crystal diffraction grating.

26. The method of claim 23, wherein said taking action comprises outputting at least one of a slurry concentration data signal and an endpoint signal.

27. The method of claim 23, wherein said predetermined material comprises metal.

28. A system for real-time measurement of trace metal concentration in a chemical mechanical polishing (CMP) slurry, comprising:
    a radiation flow cell for carrying a CMP slurry;
    a slurry pickup head coupled to the flow cell; and
    an analyzer for measuring properties of the slurry flowing through the flow cell.

29. A material concentration measurement system, comprising:
    a slurry flow cell for having a slurry flow therethrough;
    a radiation source for illuminating said slurry, such that radiation traveling through the flow cell produces fluorescence in predetermined material atoms contained in the slurry; and
    an analyzer for measuring, in real-time, a concentration of trace predetermined material atoms in the slurry in response to the fluorescence.

* * * * *